(12) United States Patent
Wright et al.

(10) Patent No.: US 11,000,486 B2
(45) Date of Patent: May 11, 2021

(54) COMBINATION OF CANNABINOIDS IN THE TREATMENT OF LEUKAEMIA

(71) Applicant: GW Research Limited, Histon (GB)

(72) Inventors: Stephen Wright, Histon (GB); Wai Liu, London (GB); Katherine Scott, London (GB); Angus Dalgleish, London (GB)

(73) Assignee: GW Research Limited, Cambridge (GB)

( * ) Notice: Subject to any disclaimer, the term of this patent is extended or adjusted under 35 U.S.C. 154(b) by 0 days.

(21) Appl. No.: 16/488,821

(22) PCT Filed: Feb. 16, 2018

(86) PCT No.: PCT/GB2018/050421
§ 371 (c)(1),
(2) Date: Aug. 26, 2019

(87) PCT Pub. No.: WO2018/154280
PCT Pub. Date: Aug. 30, 2018

(65) Prior Publication Data
US 2020/0022925 A1    Jan. 23, 2020

(30) Foreign Application Priority Data

Feb. 27, 2017 (GB) ................................. 1703115

(51) Int. Cl.
| | | |
|---|---|---|
| *A61K 31/05* | (2006.01) | |
| *A61K 31/352* | (2006.01) | |
| *A61P 35/02* | (2006.01) | |
| A61K 31/475 | (2006.01) | |
| A61K 31/7068 | (2006.01) | |

(52) U.S. Cl.
CPC ............ *A61K 31/05* (2013.01); *A61K 31/352* (2013.01); *A61P 35/02* (2018.01); *A61K 31/475* (2013.01); *A61K 31/7068* (2013.01)

(58) Field of Classification Search
CPC ........ A61K 31/05; A61K 31/352; A61P 35/02
See application file for complete search history.

(56) References Cited

FOREIGN PATENT DOCUMENTS

| KR | 20120080675 A | 7/2012 |
| WO | WO 2008/144475 A1 | 11/2008 |
| WO | WO 2016/087649 A2 | 6/2016 |

OTHER PUBLICATIONS

[No Author Listed] Database WPI Week 201252. Clarivate Analytics. Accession No. 2012-J67237. Jan. 8, 2011. 2 pages.
Gallily et al., Gamma-irradiation enhances apoptosis induced by cannabidiol, a non-psychotropic cannabinoid, in cultured HL-60 myeloblastic leukemia cells. Leuk Lymphoma. Oct. 2003;44(10):1767-73.
Kampa-Schittenhelm et al., Epigenetic hypomethylation of the 5'UTR of NADPH oxidase 4 (NOX4) by cannabidiol (CBD) results in increased protein expression, catalyzation of reactive oxygen species (ROS) and induction of apoptosis in acute leukemia. Oncol. Res. Treat. 2017;40(suppl 3):22. Abstract.
Liu et al., Enhancing the in vitro cytotoxic activity of Delta9-tetrahydrocannabinol in leukemic cells through a combinatorial approach. Leuk Lymphoma. Sep. 2008;49(9):1800-9. doi: 10.1080/10428190802239188.
Scott et al., Anticancer effects of phytocannabinoids used with chemotherapy in leukaemia cells can be improved by altering the sequence of their administration. Int J Oncol. Jul. 2017;51(1):369-377. doi: 10.3892/ijo.2017.4022. Epub May 29, 2017.
Scott et al., Enhancing the activity of cannabidiol and other cannabinoids in vitro through modifications to drug combinations and treatment schedules. Anticancer Res. Oct. 2013;33(10):4373-80.
Singh et al., Cannabis extract treatment for terminal acute lymphoblastic leukemia with a Philadelphia chromosome mutation. Case Rep Oncol. Sep.-Dec. 2013; 6(3): 585-592. EPub Nov. 28, 2013. doi: 10.1159/000356446.
Velasco et al., Anticancer mechanisms of cannabinoids. Curr Oncol. Mar. 2016; 23(Suppl 2): S23-S32. EPub Mar. 16, 2016. doi: 10.3747/co.23.3080.
GB 1703115.4, Dec. 8, 2017, Combined Search and Examination Report.
PCT/GB2018/050421, Apr. 20, 2018, International Search Report and Written Opinion.
PCT/GB2018/050421, Sep. 6, 2019, International Preliminary Report on Patentability.

*Primary Examiner* — Samira J Jean-Louis
(74) *Attorney, Agent, or Firm* — Wolf, Greenfield & Sacks, P.C.

(57) ABSTRACT

The present invention relates to the use of a combination of two different cannabinoids in the treatment of leukaemia. The combination of CBD with THC appears to be particularly effective in reducing cell number in this disease. Preferably the cannabinoids are used in the form of an extract of *Cannabis* such that many of the naturally occurring compounds are co-extracted with the THC or CBD. Alternatively, the cannabinoids are present in the form of a highly purified extract of *Cannabis*, wherein the CBD or THC are present at greater than 98% of the total extract (w/w) and the other components of the extract are characterised. Alternatively, the CBD and THC may be synthetically produced. A specific ratio of CBD and THC such as 10:1 to 1:10 (CBD:THC) or more preferably between 2:1 to 1:2 (CBD:THC) may be used.

18 Claims, 4 Drawing Sheets

COMBINATION OF CANNABINOIDS IN THE TREATMENT OF LEUKAEMIA

RELATED APPLICATION

This application is a national stage filing under 35 U.S.C. 371 of International Patent Application Serial No. PCT/GB2018/050421, filed Feb. 16, 2018, the entire contents of which is incorporated by reference herein in its entirety.

FIELD OF THE INVENTION

The present invention relates to the use of a combination of two different cannabinoids in the treatment of leukaemia. The combination of CBD with THC appears to be particularly effective in reducing cell number in this disease.

Preferably the cannabinoids are used in the form of an extract of *Cannabis* such that many of the naturally occurring compounds are co-extracted with the THC or CBD. Alternatively, the cannabinoids are present in the form of a highly purified extract of *Cannabis*, wherein the CBD or THC are present at greater than 98% of the total extract (w/w) and the other components of the extract are characterised. Alternatively, the CBD and THC may be synthetically produced. A specific ratio of CBD and THC such as 10:1 to 1:10 (CBD:THC) or more preferably between 2:1 to 1:2 (CBD:THC) may be used.

In a further embodiment of the invention the CBD and THC are used in combination with a chemotherapeutic agent to treat the leukaemia. It has been found that the cannabinoid-pair CBD and THC can work synergistically with the chemotherapeutic agent vincristine or cytarabine to reduce cell number and viability. The CBD-THC pair may be formulated for administration separately, sequentially (including before and/or after), or simultaneously with one or more chemotherapeutic drugs or the combination may be provided in a single dosage form. Where the CBD+THC pair may be formulated for administration separately, sequentially or simultaneously to the chemotherapeutic agent, it may be provided as a kit or together with instructions to administer the one or more components in the manner indicated. It may also be used as the sole medication, i.e. as a monotherapy.

BACKGROUND TO THE INVENTION

Leukaemia is a group of cancers that usually begin in the bone marrow and result in high numbers of abnormal white blood cells. Symptoms include bleeding and bruising problems, feeling tired, fever, and an increased risk of infections. Symptoms occur due to a lack of normal blood cells. Diagnosis is typically made by blood tests or bone marrow biopsy.

The exact cause of leukaemia is unknown. Different kinds of leukaemia are believed to have different causes. Both inherited and environmental factors are believed to be involved. Risk factors include smoking, ionizing radiation, some chemicals (such as benzene), prior chemotherapy, and Down syndrome. People with a family history of leukaemia are also at higher risk.

There are two main types of leukaemia: lymphoblastic leukaemia and myeloid leukaemia, each type can be split into acute sub-types, such as acute lymphoblastic leukaemia (ALL) and acute myeloid leukaemia (AML), and chronic sub-types such as chronic lymphoblastic leukaemia (CLL) and chronic myeloid leukaemia (CML).

A model for lymphoblastic leukaemia is the CEM cell line which more specifically is an acute model and a model for the myeloid leukaemia is the HL60 cell line which again is an acute model.

Treatment for leukaemia often involves a combination of chemotherapy, radiation therapy, targeted therapy, and bone marrow transplant. The success of treatment depends on the type of leukaemia and the age of the person.

Leukaemia is the most common type of cancer in children, with three quarters of cases in children being the acute lymphoblastic type. However, about 90% of all leukaemias are diagnosed in adults, with AML and CLL being most common in adults.

The type of chemotherapeutic drug used to treat leukaemia often depends upon the type of disease that has been diagnosed.

In acute lymphoblastic leukaemia (ALL) the chemotherapy medicines used include: asparaginase, blinatumomab, clofarabine, daunorubicin, doxorubicin, methotrexate, nelarabine, or vincristine. Corticosteroids such as dexamethasone or prednisone are also often administered.

In acute myelogenous leukaemia (AML) the chemotherapy medicines used include: cytarabine, daunorubicin, idarubicin, or mitoxantrone.

In chronic lymphocytic leukaemia (CLL) the chemotherapy medicines bendamustine, chlorambucil, cyclophosphamide, fludarabine, or vincristine are often used, these are often used in addition to corticosteroids, such as prednisone, and monoclonal antibodies, such as alemtuzumab or rituximab.

In chronic myeloid leukaemia (CML) the chemotherapy medicines cyclophosphamide or cytarabine are commonly used in addition to tyrosine kinase inhibitors such as dasatinib, imatinib, or nilotinib.

There are a number of side effects associated with chemotherapeutic medications; these include nausea and vomiting, fatigue, hair loss, pain, sore mouth and throat, diarrhoea, nervous system disorders and blood disorders. These side effects can be so severe and can have such an impact on a patient's quality of life they may wish to stop treatment even though this may shorten their life.

There is growing evidence to support a role for cannabinoids in cancer therapy. Their effects in the induction of cell death, inhibition of proliferation and anti-metastatic activity in different human cancer in vitro and in vivo models have been documented (Velasco et al., 2016).

The most relevant effect of cannabinoids in cancer was investigated with tetrahydrocannabinol (THC) and cannabidiol (CBD). THC and CBD were able to reduce cell proliferation and induce autophagic-dependent cell death in glioblastoma (GBM), hepatocellular carcinoma, melanoma and breast cancer.

THC has been demonstrated to interact with existing anti-leukaemia therapies. Synergistic interactions between THC and cytarabine, doxorubicin and vincristine on the cell viability in a leukaemia cell line was shown (Liu et al., 2008).

Additionally, certain cannabinoids may act synergistically in reducing cell viability in leukaemia cell lines. Here the cannabinoids CBD, cannabigerol (CBG) and cannabigervarin (CBGV) and their acid forms were tested alone or in some combinations (Scott et al., 2013).

A single patient study published in 2013 described a patient with acute lymphoblastic leukaemia which resulted in a decrease in blast cell count after treatment with *Cannabis* oil. It was not known what the composition or content of the cannabinoids in the *Cannabis* oil was.

The present invention demonstrates the synergy of a combination of CBD and THC in the reduction of cell numbers in leukaemia cell lines. Furthermore, the present invention demonstrated that the cannabinoid-pair CBD and THC were further able to act synergistically to reduce cell number and cell viability in leukaemia cell lines. In particular the combination of CBD+THC with vincristine was of particular significance. This surprising result would enable a lower or sub-effective dose of the chemotherapeutic to be used.

BRIEF SUMMARY OF THE DISCLOSURE

In accordance with a first aspect of the present invention there is provided a combination of cannabidiol (CBD) and tetrahydrocannabinol (THC) for use in the treatment of leukaemia.

In one embodiment the leukaemia is lymphoblastic leukaemia. Preferably the lymphoblastic leukaemia is acute lymphoblastic leukaemia (ALL) or chronic lymphoblastic leukaemia (CLL).

In a further embodiment the leukaemia is myeloid leukaemia. Preferably the myeloid leukaemia is acute myeloid leukaemia (AML) or chronic myeloid leukaemia (CML).

In a further embodiment the leukaemia is a childhood leukaemia.

Preferably the CBD and/or THC are present in the form of at least one extract from at least one *Cannabis* plant. The *Cannabis* plant(s) preferably include at least one *Cannabis* chemovar. Most preferably the plant extract will be a botanical drug substance (BDS), as defined herein.

The CBD and/or the THC may be present as a highly purified extract of *Cannabis* which comprises at least 98% (w/w) of the particular cannabinoid. Alternatively, the CBD and/or the THC are present as a synthetic compound.

The CBD and THC are preferably present in a ratio of from 10:1 to 1:10 (CBD:THC). More preferably the CBD and THC are present in a ratio of from 5:1 to 1:5 (CBD:THC), through 2:1 to 1:2 (CBD:THC), 1.08:1 to 1:1.08 (CBD:THC) to approximately 1:1 (CBD:THC).

The CBD and THC are preferably present in a combined dose of from 0.1 to 100 mg/kg/day. In certain circumstances where greater doses of cannabinoids are required the amount of cannabinoid present are in a dose of 0.1 to 100 mg/kg/day per cannabinoid.

In a further embodiment of the present invention the combination of CBD and THC further comprises a chemotherapeutic drug.

Preferably the chemotherapeutic drug is: cytarabine or vincristine.

Preferably where the chemotherapeutic drug is vincristine the type of leukaemia to be treated is lymphoblastic leukaemia.

Alternatively, where the chemotherapeutic drug is cytarabine the type of leukaemia to be treated is myeloid leukaemia.

Preferably the CBD and THC are administered separately, sequentially or simultaneously to the chemotherapeutic drug.

Preferably the CBD and THC are administered sequentially before the chemotherapeutic drug. Alternatively, the CBD and THC are administered sequentially after the chemotherapeutic drug. Indeed, the CBD and THC may be administered sequentially before and after the chemotherapeutic drug.

The dose of chemotherapeutic drug may be provided at sub-effective or sub-optimal levels in order to reduce the side effects associated with chemotherapeutic agents.

Preferably the dose of chemotherapeutic drug is reduced by at least 20% of the therapeutically effective dose when used alone, more preferably the dose is reduced by at least 50% of the therapeutically effective dose when used alone. Where the cannabinoids are able to work in a statistically significant manner the dose of chemotherapeutic drug may even be reduced by at least 100% or even at least 200% or more of the therapeutically effective dose when used alone.

Preferably, the CBD and THC which may further comprise a chemotherapeutic drug is formulated as a pharmaceutical composition further comprising one or more pharmaceutically acceptable carriers, excipients or diluents. The composition may be formulated into pharmaceutical dosage forms which may contain other pharmaceutically acceptable excipients for modifying conditions such as pH, osmolarity, taste, viscosity, sterility, lipophilicity, solubility etc. The choice of diluents, carriers or excipients will depend on the desired dosage form, which may in turn be dependent on the intended route of administration to a patient.

In accordance with a second aspect of the present invention there is provided a method of treating leukaemia comprising administering cannabidiol (CBD) and tetrahydrocannabinol (THC) to a subject in need thereof. Preferably the subject is a human.

Preferably the method of treatment further comprises a chemotherapeutic drug, particularly vincristine or cytarabine. More preferably the CBD and THC are administered separately, sequentially or simultaneously to the chemotherapeutic drug.

Definitions

Definitions of some of the terms used to describe the invention are detailed below:

The cannabinoids described in the present application are listed below along with their standard abbreviations.

TABLE 1

Cannabinoids and their abbreviations

CBD  Cannabidiol

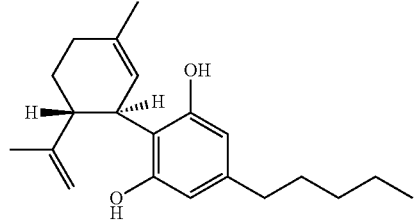 [SMILES: C=C(C)[C@@H]1CCC(C)=C[C@H]1c1c(O)cc(CCCCC)cc1O]

THC  Tetrahydro-cannabinol

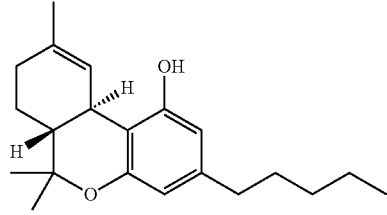 [SMILES: CCCCCc1cc(O)c2c(c1)OC(C)(C)[C@@H]1CCC(C)=C[C@@H]21]

CBG  Cannabigerol

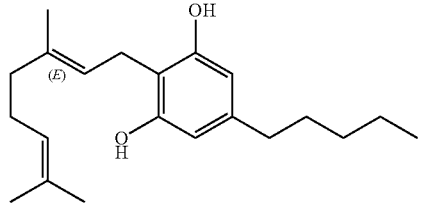 [SMILES: CCCCCc1cc(O)c(C/C=C(\C)CCC=C(C)C)c(O)c1]

The table above is not exhaustive and merely details the cannabinoids which are identified in the present application for reference. So far over 60 different cannabinoids have been identified and these cannabinoids can be split into different groups as follows: Phytocannabinoids; Endocannabinoids and Synthetic cannabinoids (which may be novel cannabinoids or synthetically produced phytocannabinoids or endocannabinoids).

"Phytocannabinoids" are cannabinoids that originate from nature and can be found in the *Cannabis* plant. The phytocannabinoids can be isolated from plants to produce a highly purified extract or can be reproduced synthetically.

A "plant extract" is an extract from a plant material as defined in the Guidance for Industry Botanical Drug Products Draft Guidance, August 2000, US Department of Health and Human Services, Food and Drug Administration Centre for Drug Evaluation and Research.

In the context of this application the terms "*Cannabis* extract" or "extract from a *Cannabis* plant", which are used interchangeably, encompass "Botanical Drug Substances" derived from *Cannabis* plant material. A Botanical Drug Substance is defined in the Guidance for Industry Botanical Drug Products Draft Guidance, August 2000, US Department of Health and Human Services, Food and Drug Administration Centre for Drug Evaluation and Research as: "A drug substance derived from one or more plants, *algae*, or macroscopic *fungi*. It is prepared from botanical raw materials by one or more of the following processes: pulverisation, decoction, expression, aqueous extraction, ethanolic extraction, or other similar processes." A botanical drug substance does not include a highly purified or chemically modified substance derived from natural sources. Thus, in the case of *Cannabis*, "botanical drug substances" derived from *Cannabis* plants do not include highly purified, Pharmacopoeial grade cannabinoids.

"Botanical drug substances" derived from *Cannabis* plants include primary extracts prepared by such processes as, for example, maceration, percolation, extraction with solvents such as C1 to C5 alcohols (e.g. ethanol), Norflurane (HFA134a), HFA227 and liquid carbon dioxide under sub-critical or super-critical conditions. The primary extract may be further purified for example by super-critical or sub-critical solvent extraction, vaporisation or chromatography. When solvents such as those listed above are used, the resultant extract contains non-specific lipid soluble material. This can be removed by a variety of processes including "winterisation", which involves chilling to −20° C. followed by filtration to remove waxy ballast, extraction with liquid carbon dioxide and by distillation.

In embodiments wherein, the cannabinoids are provided as a BDS, the BDS is preferably obtained by $CO_2$ extraction, under sub-critical or super-critical conditions, followed by a secondary extraction, e.g. an ethanolic precipitation, to remove a substantial proportion of waxes and other ballast. This is because the ballast includes wax esters and glycerides, unsaturated fatty acid residues, terpenes, carotenes, and flavonoids which are not very soluble in the chosen solvent/co-solvent, particularly the preferred co-solvent, propylene glycol, and will precipitate out. Most preferably the BDS is produced by a process comprising decarboxylation, extraction with liquid carbon dioxide and then a further extraction to remove significant amounts of ballast. Most preferably the ballast is substantially removed by an ethanolic precipitation.

Most preferably, *Cannabis* plant material is heated to a defined temperature for a defined period of time in order to decarboxylate cannabinoid acids to free cannabinoids prior to extraction of the BDS.

Botanical drug substances are formulated into "Botanical Drug Products" which are defined in the Guidance for Industry Botanical Drug Products Draft Guidance, August 2000, US Department of Health and Human Services, Food and Drug Administration Centre for Drug Evaluation and Research as: "A botanical product that is intended for use as a drug; a drug product that is prepared from a botanical drug substance."

"*Cannabis* plants" includes wild type *Cannabis* sativa and variants thereof, including *Cannabis* chemovars which naturally contain different amounts of the individual cannabinoids.

In the present invention a BDS is considered to have two components: the phytocannabinoid-containing component and the non-phytocannabinoid containing component. Preferably the phytocannabinoid-containing component is the larger component comprising greater than 50% (w/w) of the total BDS and the non-phytocannabinoid containing component is the smaller component comprising less than 50% (w/w) of the total BDS.

A typical extract of *Cannabis* is Sativex, this medication may contain in a 1 ml vol: THC 25-50 mg/ml, preferably 27 mg/ml (based on amount of cannabinoid in a botanical drug substance), CBD 25-50 mg/ml, preferably 25 mg/ml (based on amount of cannabinoid in a botanical drug substance), propylene glycol 0.5 ml/ml, peppermint oil 0.0005 ml/ml, and ethanol (anhydrous) qs to 1 ml.

"Highly purified cannabinoid extracts" are defined as cannabinoids that have been extracted from the *Cannabis* plant and purified to the extent that other cannabinoids and non-cannabinoid components that are co-extracted with the cannabinoids have been substantially removed, such that the highly purified cannabinoid is greater than or equal to 98% (w/w) pure.

"Synthetic cannabinoids" are compounds that have a cannabinoid or cannabinoid-like structure and are manufactured using chemical means rather than by the plant.

Phytocannabinoids can be obtained as either the neutral (decarboxylated form) or the carboxylic acid form depending on the method used to extract the cannabinoids. For example, it is known that heating the carboxylic acid form will cause most of the carboxylic acid form to decarboxylate into the neutral form.

The therapeutically effective dose of vincristine ranges from 0.4 to 1.4 $mg/m^2$. The standard dose of vincristine used to treat leukaemia is 1.4 $mg/m^2$ administered by IV once per week.

The therapeutically effective dose of cytarabine ranges from 100 to 200 $mg/m^2$. The standard dose of cytarabine used to treat leukaemia is 100 $mg/m^2$ administered by continuous IV over 24 hours, once per fortnight.

To express a $mg/m^2$ dose as the equivalent mg/kg. dose, divide the dose by the appropriate km factor. In adult humans where the km factor is 37 the calculation for 100 $mg/m^2$ would be: 100 $mg/m^2$/37=2.7 mg/kg A "sub-optimal" or "sub-effective" dose of chemotherapeutic drug refers to a lower dose than the therapeutically effective dose.

BRIEF DESCRIPTION OF THE DRAWINGS

Embodiments of the invention are further described hereinafter with reference to the accompanying drawings, in which.

LEGENDS TO THE FIGURES

Figure 1:
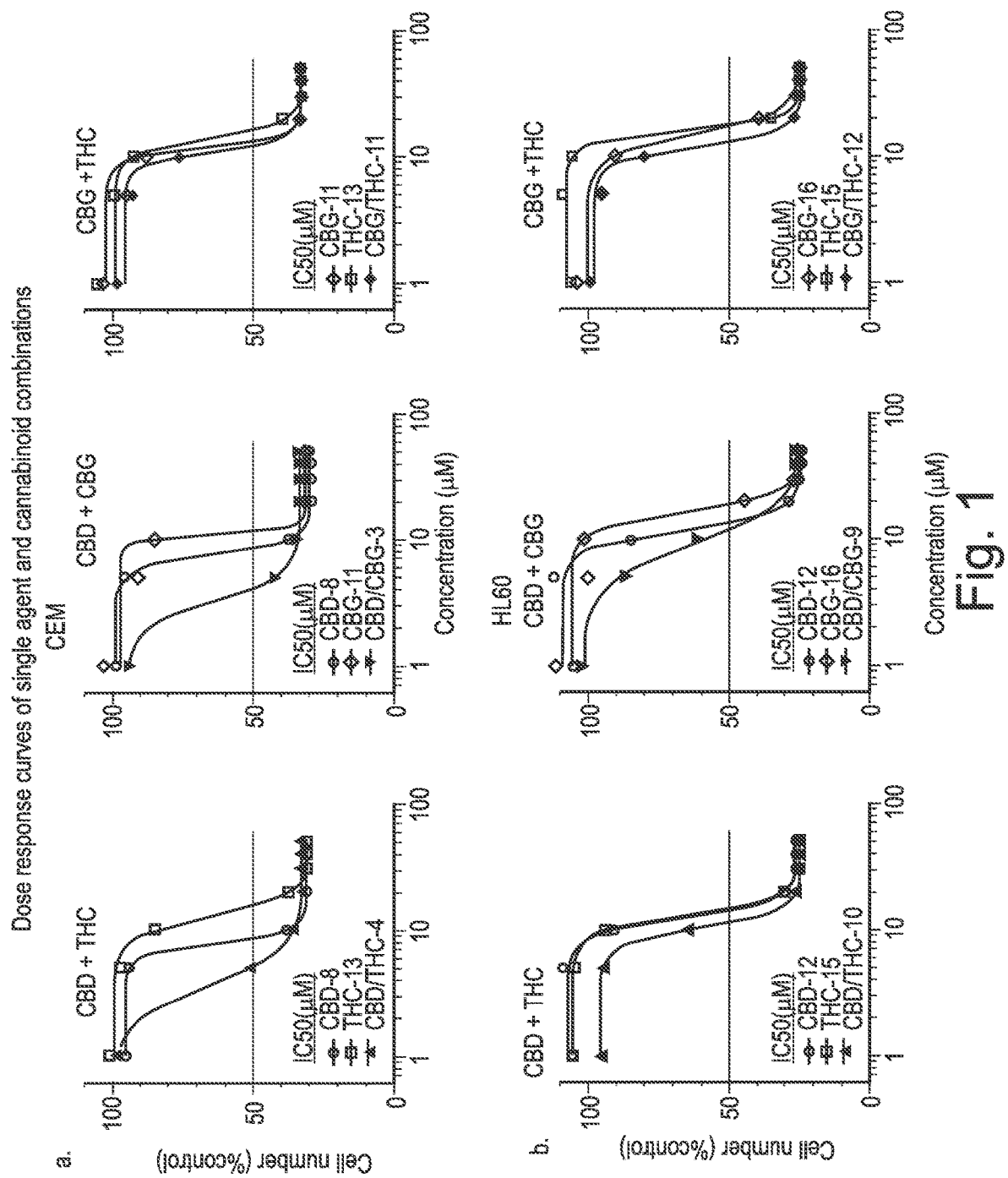
FIG. 1 shows the dose response curves of single agent and cannabinoid combinations.

FIG. 1. Dose response curves of single agent and cannabinoid combinations. CEM and HL60 cells were grown for 48 hr in the presence of increasing concentrations of the three cannabinoids, THC, CBD and CBG, either as single agents or in dual combinations prepared at a 1:1 ratio. Thus 10 µM of the CBD and THC combination would be made of 5 µM CBD+5 µM THC. Cell number was assessed using the MTT assay and the concentration required to reduce the cell number by 50% (IC50) for each condition in CEM (a) and HL60 (b) was calculated using GraphPad Prism. Each data point represents the mean of at least three separate experiments. SDs have been omitted for clarity.

Figure 2:
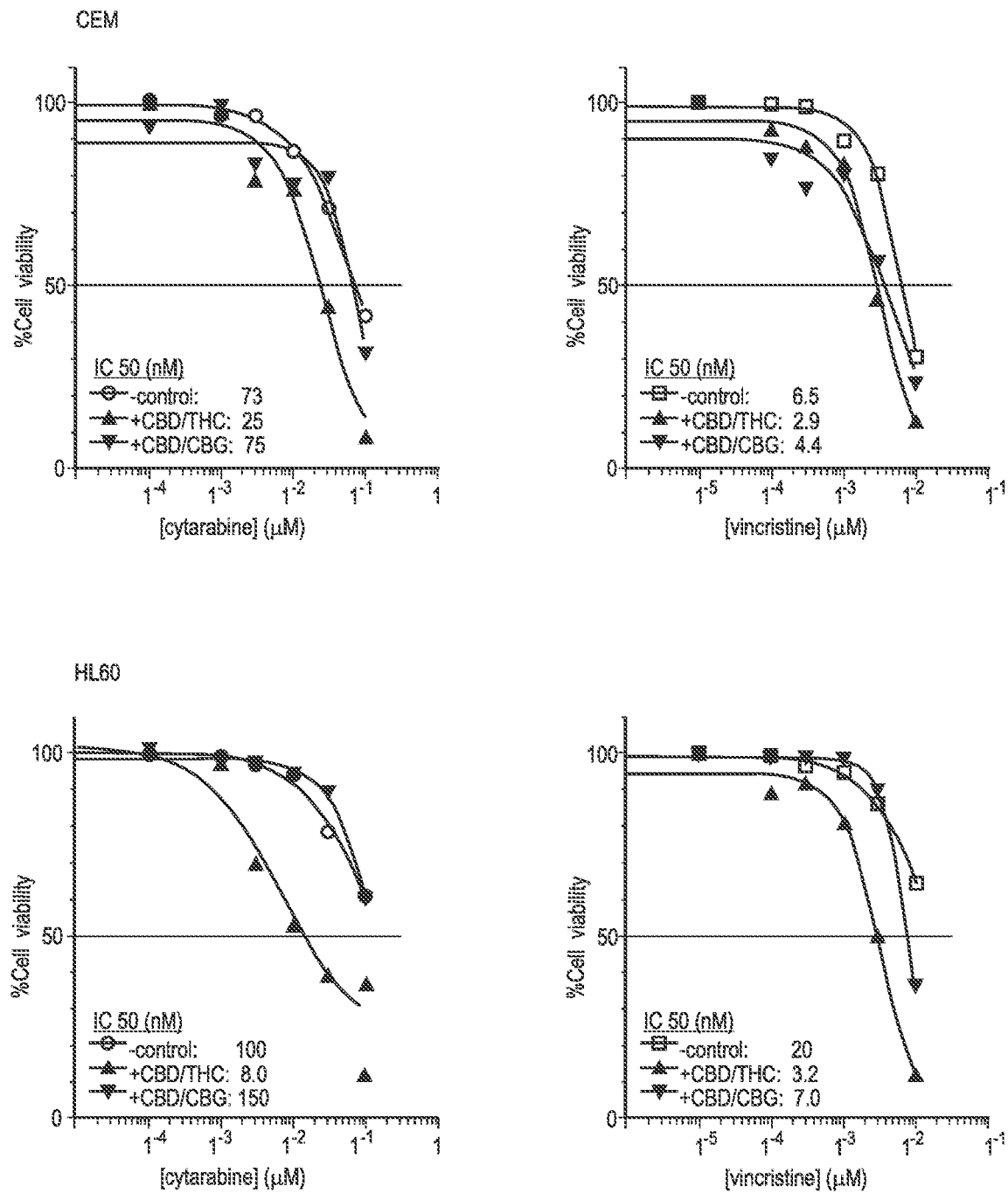
FIG. 2 shows the effect of low doses of cannabinoids in sensitising chemotherapy treatment.

FIG. 2. Sensitising chemotherapy action with low doses of cannabinoids. CEM and HL60 cells were grown for 72 hr in the presence of increasing concentrations of cytarabine (CYT) or vincristine (VIN). The effect of a low dose of CBD/THC or CBD/CBG on the activity of CYT and VIN was also assessed. IC50 values for percentage cell viability were determined by emax models.

Figure 3:
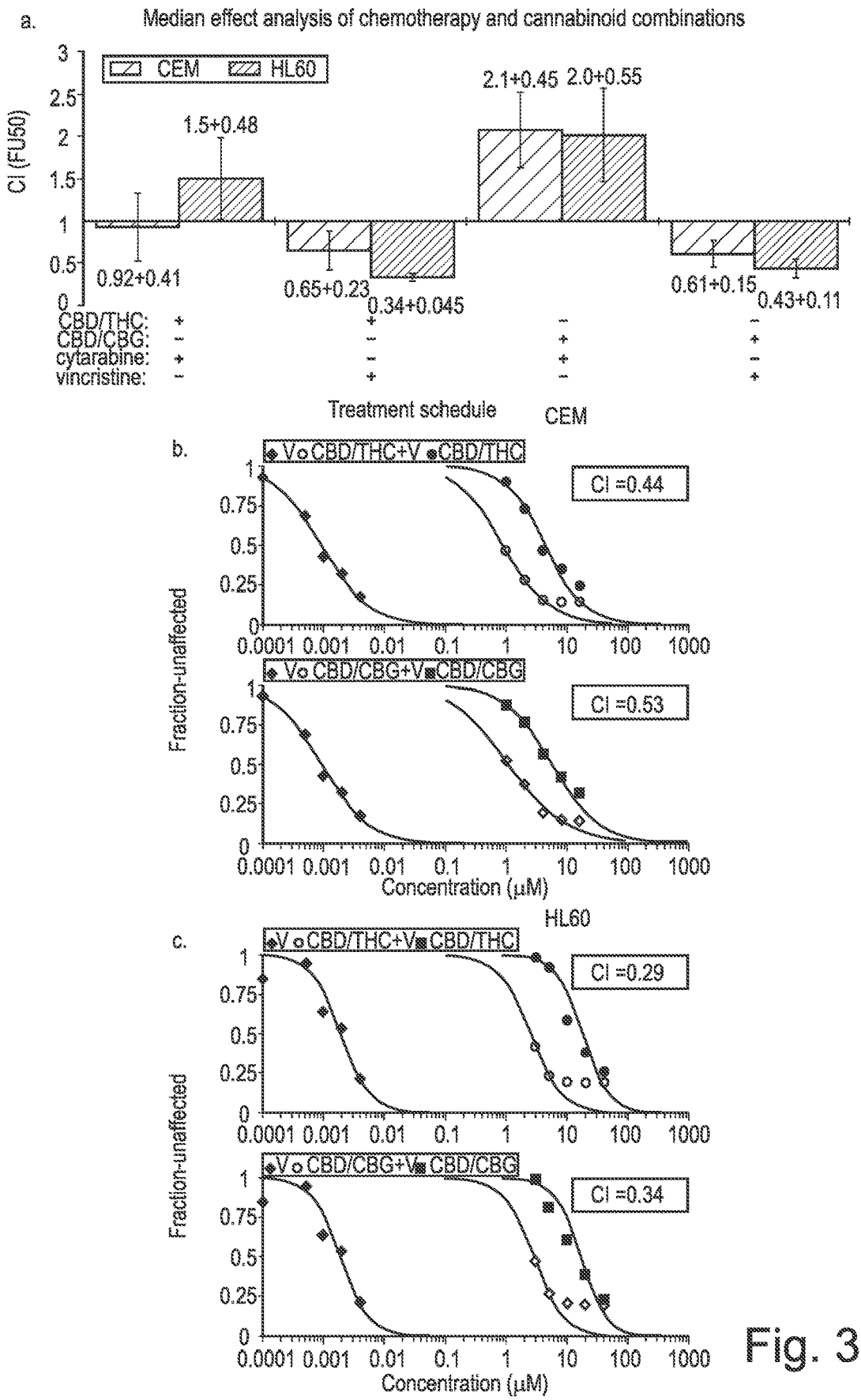
FIG. 3 shows the median effect analysis of chemotherapy and cannabinoid combinations.

FIG. 3. Median effect analysis of chemotherapy and cannabinoid combinations. CEM and HL60 cells were grown for 72 hr in the presence of increasing concentrations of both cytarabine or vincristine and a cannabinoid-pair, combined at fractions of their respective IC50s. CBD/THC and CBD/CBG were the two cannabinoid-pairs that were investigated, and were used at equal 1:1 ratios. Cell number was assessed at 72 hr using the MTT assay and defined algorithms were then used to generate a combination index score (CI) which indicates the nature of the combination interactions (CI=1=additivity; CI<1=synergy; CI>1=antagonism) (a). Representative data have also been included from experiments in CEM (b) and HL60 (c) for the cannabinoid-pairs with vincristine. Each data point in the column graph represents the mean and SD of at least three separate experiments.

Figure 4:
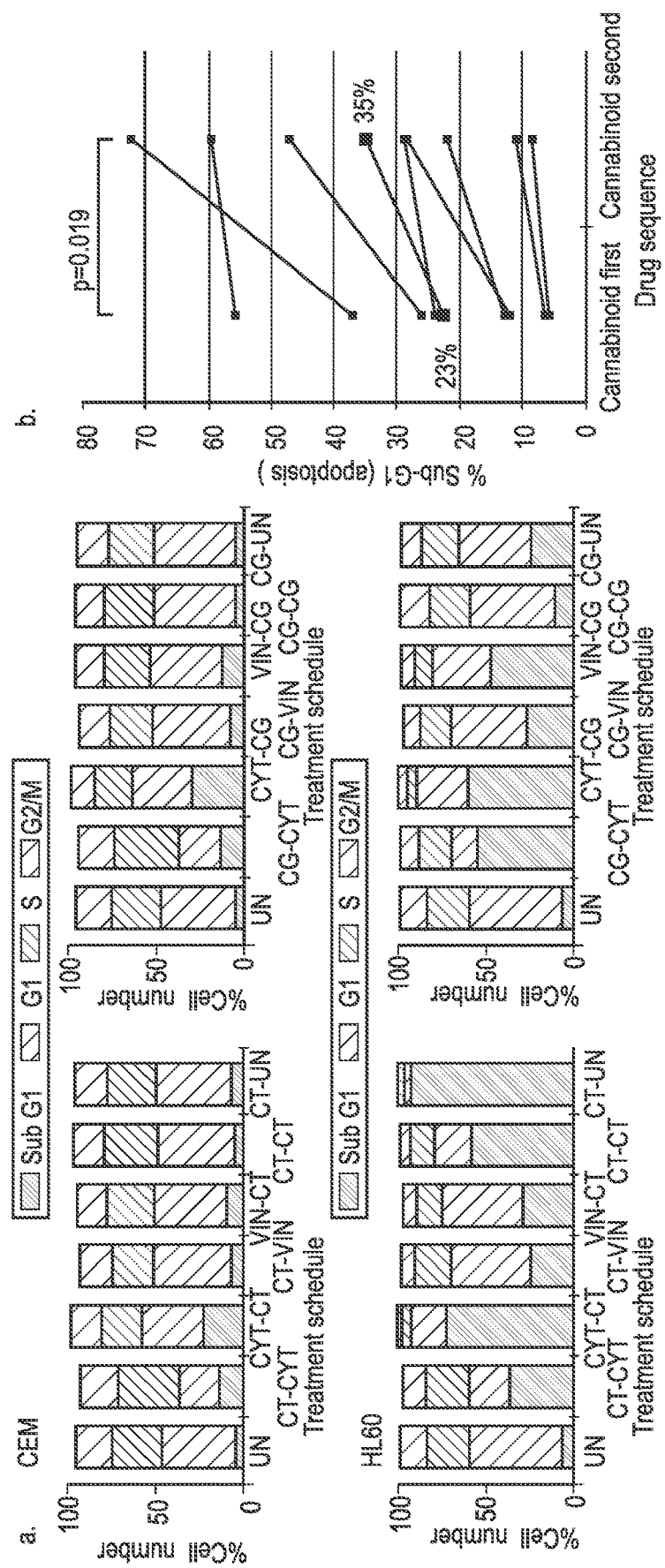
FIG. 4 shows the effect of drug sequence on the cell cycle.

FIG. 4. Effect of drug sequence on the cell cycle. CEM and HL60 cells were cultured according to schedules consisting two distinct treatment stages lasting 48 hr each. Treatments consisted of a cannabinoid—CBD+THC (CT) or CBD+CBG (CG) in the first stage, followed by cytarabine (CYT) or vincristine (VIN) in the second. Parallel cultures were also performed in which the sequence of drugs was reversed. Cell cycle distribution was then assessed by flow cytometry at 96 hr (a). The specific effect on % sub-G1 cells where a cannabinoid was used first was compared with those in which a cannabinoid was used second (b).

DETAILED DESCRIPTION

The following examples demonstrate the effects of combinations of cannabinoids on leukaemia cells lines and also the effects of cannabinoid-pairs in combination with chemotherapeutic drugs used in the treatment of leukaemia.

Synergistic effects are calculated using combination interactions (CI), where a CI equal to 1 indicates an additive effect, a CI of less than 1 demonstrates synergistic interactions of compounds and a CI of greater than 1 indicates that the two compounds are working antagonistically. Where compounds are shown to work synergistically there is a suggestion that such a combination will produce beneficial effects in use.

Such beneficial effects include a lower or sub-optimal dose of the compounds being required to produce the same effect were only one of the compounds used. This is of benefit particularly where one or more of the compounds produce side effects meaning that at lower dose side effects are reduced or removed. Further benefits that occur are that the effect produced is larger, for example the combination may produce a greater reduction in cell viability which is of particular benefit in the treatment of a cancer.

Conversely if the CI value is indicative of an antagonistic effect it would be unwise to combine the two compounds for use in the treatment of a disease, particularly a disease such as cancer. When compounds work antagonistically they can cancel the effects of each other out, thereby reducing the effectiveness of each compound. Clearly this is not a useful treatment option.

The section below describes the general methodology used in the four Examples.

General Materials and Methodology
Cell Culture and Drugs

The human cancer cell lines CEM (acute lymphocytic leukaemia) and HL60 (promyelocytic leukaemia) used (European Collection of Authenticated Cell Cultures, Salisbury, UK), and grown in RPMI-1640 medium (Sigma-Aldrich Company Ltd., Dorset, UK) supplemented with 10% foetal bovine serum (FBS) and 2 mM L-glutamine. All cell lines were incubated in a humidified atmosphere with 5% $CO_2$ in air at 37° C., and discarded after ~12 passages.

Cytarabine (CYT), (Sigma) and vincristine (VIN), (Sigma) were reconstituted in PBS at a stock concentration of 10 mM, and kept at −20° C. for no more than four weeks.

Cannabidiol (CBD), cannabigerol (CBG) and tetrahydrocannabinol (THC) were dissolved in ethanol to appropriate concentrations that ensured a final ethanol concentration in cell cultures <0.1%.

For experiments with cannabinoids, the amount of FBS in the cell culture medium was reduced to 5%.

One aim of the current study was to investigate the benefit of using two different cannabinoids in combination. Cannabinoids were paired concomitantly at a 1:1 ratio, where the stated concentration for them reflected an equal amount of each cannabinoid-component; for example, 10 µM CBD+THC contained 5 µM CBD and 5 µM THC.

Proliferation Assays—Cannabinoids Alone

To study the effect of the cannabinoids on cell growth, leukaemia cells that were growing exponentially were seeded into 96-well plates at a density of $1.5 \times 10^4$/well. Cannabinoids were then added to the wells at various concentrations, ensuring an equal volume of 200 µl across the plate.

Single-agent testing: Either CBD, CBG or THC alone was added to the wells at a concentration range of 1-50 µM.

Paired-cannabinoid testing CBD+CBG, CBD+THC or CBG+THC were added to the wells at a concentration range for the paired cannabinoids of 1-50 µM. The molarity was based upon the total cannabinoids in each pair.

Cell number was assessed after 48 h using a methylthiazoletetrazolium (MTT)-based assay.

Combination Studies—Median-Effect Analysis

Cells ($1.5 \times 10^4$/well) growing exponentially were reset in fresh culture medium and aliquoted into 96-well plates. A cannabinoid-pair (either CBD+THC or CBD+CBG) was combined with CYT or VIN at concentrations that were equal ratios of their respective IC50.

Cell number was then assessed after 72 h by the MTT-based assay, and a combination index (CI) calculated by using the median-effect equation.

Combination Studies—Modulatory Effect

The ability of cannabinoids to modify the efficacy CYT and VIN was studied by assessing and comparing the IC50 of the anti-leukaemia drugs in the absence and presence of the cannabinoids.

The cannabinoids tested were CBD+CBG and CBD+THC, and these were used at a single total sub-optimal concentration of 1 µM in CEM and 5 µM HL60.

Methodologically, cells ($5 \times 10^4$/well) growing exponentially were reset in fresh culture medium and aliquoted into 96-well plates. Drugs were added (CYT and VIN over a range of concentrations) and cell number determined after 72 h.

Parallel 6-well plates containing cells were also prepared and were cultured with the same treatment combinations described. These allowed for determination of cell cycle distribution at 72 h by flow cytometry utilising the nucleic acid stain propidium iodide.

Combination Studies—Drug Sequence and the Impact of a Recovery Phase

CEM and HL60 cells were seeded into 6-well plates at a density of $1 \times 10^5$/well and then treated according to a culture schedule that lasted a total of 96 h.

The treatment would involve two separate phases; each lasting 48 h. One set of drugs would be administered in the first 48 h phase and a second set of drugs in the following 48 h phase. The culture medium would be removed by centrifugation after the first treatment to be replaced with fresh medium in an attempt to remove the drugs used in the first phase of treatment. The drugs studied were either: CBD+CBG (4 µM in CEM and 10 µM in HL60), CBD+THC (4 µM in CEM and 10 µM in HL60), CYT (10 nM), or VIN (0.1 nM).

The effect of a recovery phase was assessed by keeping the second 48 h phase of treatment drug-free. Flow cytometry using propidium iodide staining was performed at the end of the experiment to assess the extent of cell death/apoptosis.

Immunoblotting Analysis

Western blot analyses were performed. Primary antibody probing was performed with anti-cyclin B1 and anti-GAPDH (New England Biolabs, Hitchin, UK) and used at a dilution of 1:1,000.

Appropriate HRP-conjugated secondary antibodies were then used (New England Biolabs), and bands were visualised by the ECL-plus detection system (Amersham Biosciences Ltd., Little Chalfont, UK).

Statistical Analysis

All statistical analyses were performed using GraphPad Prism or Microsoft Excel, and differences between treatments and control groups were determined by analysis of variance and subsequently by paired tests. Data values were presented as the means and SDs of at least three separate experiments.

Example 1

Efficacy of Combinations of Cannabinoids in Two Leukaemia Cell Lines

This example paired CBD, CBG and THC in different permutations, and assessed their effects on cell numbers in two different cell lines after 48 h of treatment.

IC50 values for the individual cannabinoids were determined, and these were compared with the IC50 achieved when the matching cannabinoid-pair were used. Data from these experiments are shown in FIG. 1a (CEM cell line) and FIG. 1b (HL60 cell line).

In the CEM cell line CBD alone had an IC50 of 7.8±0.21 µM and THC alone had an IC50 of 13±0.49 µM. When CBD and THC were combined at a ratio of 1:1 an IC50 of 3.6±0.19 µM was obtained. A reduction of the IC50 by half, in the case of CBD, and two thirds in the case of THC was surprising. It would not be expected that a sub-optimal concentration of both compounds could produce the same reduction in cell number, thereby demonstrating a synergistic effect.

The combination of CBD with THC provided a greater reduction in cell number than the other combinations of CBD with CBG or THC with CBG. Furthermore, the CEM cell line appeared to be more responsive to treatments with the cannabinoids.

Example 2

Ability of Cannabinoid-Pairs to Sensitise Leukaemia Cell Lines to the Effects of Chemotherapeutic Agents This experiment was designed to test the ability of a cannabinoid-pair to sensitise cells to the effects of CYT or VIN. The results of these are demonstrated in FIG. 2.

The ability of a sub-effective concentration of cannabinoid to alter the efficacy of CYT or VIN was determined by comparing the IC50s of the chemotherapy agents in the absence or presence of the cannabinoid-pair.

FIG. 2 demonstrates that the cannabinoid-pair CBD+THC were able to modulate the chemotherapeutics ability to reduce cell viability. For example, in the HL60 cell line the IC50 for cytarabine was 100 nM; however, this was significantly reduced to 8 nM if CBD+THC were added in combination to the chemotherapeutic. However, the addition of CBD+CBG appeared to be antagonistic as the IC50 of cytarabine increased to 150 nm when this cannabinoid-pair was used in combination.

Similar data were produced when the cannabinoid-pair CBD+THC were provided in combinations with vincristine, where a synergistic interaction led to reduced cell viability.

Example 3

Efficacy of Combinations of Cannabinoid-Pairs with Chemotherapeutic Agents in Two Leukaemia Cell Lines Median-effect analyses were employed to assess the interactions between each cannabinoid-pairs and two chemotherapeutic drugs commonly used in the treatment of leukaemia, vincristine (VIN) and cytarabine (CYT).

Cannabinoid-pairs, CBD+CBG and CBD+THC, were combined with either CYT or VIN. CI-values were then calculated by using these results and used as a way of understanding the drug-interactions (Chou, 2006). FIGS. 3a to c detail the data produced.

The combination of the cannabinoid-pair CBD+THC with vincristine produced CI values of less than 1 in both the CEM and HL60 cell lines, suggesting that this combination is synergistic.

Combinations of the cannabinoid-pair CBD+THC with cytarabine however did not appear to be synergistic, more-over the cannabinoid-pair CBD+CBG with cytarabine appeared to be antagonistic as is shown in FIG. 3a.

These data show that in when particular combinations are used, an equivalent level of action can be obtained even though the concentrations of the agents used are much lower. For example, the cannabinoid-pair CBD+THC when used in combination with VIN produced a synergistic response when used at sub-effective levels of ~2.5 µM and ~0.25 nM, respectively.

Example 4

Sequential Administration of Cannabinoid-Pairs and Chemotherapeutic Agents

Having seen synergistic interactions between cannabinoid-pairs and chemotherapeutic, when they were administered simultaneously, the impact of using the drugs sequentially was assessed.

Cells were cultured according to schedules that consisted of two rounds of treatment, each lasting 48 hrs. Each round of treatment was separated by a washing step to remove drug from the medium.

The order in which the drugs were administered was swapped in equivalent experiments to assess the counter-order of drugs. In some cases, a treatment schedule could involve the use of a cannabinoid-pair in the first round of treatment followed by no treatment in the second. This mimicked a "recovery" schedule.

Results showed that, generally, the percentage of cells within the sub-G1 population of the cell cycle were low in CEM cells following any treatments (FIG. 4a); however, the order of administration of the drugs affected the number of cells in sub-G1.

Typically, using the chemotherapeutic agent prior to administration of the cannabinoid-pair resulted in a greater number of cells in sub-G1 compared to schedules in which the order of drugs was reversed (FIG. 4a).

In HL60 cells, % sub-G1 was 37% if CBD+THC was used before CYT, but 72% if CBD+THC was used after CYT.

Furthermore, paired t-test of all the data, irrespective of cell line and drug used, showed that significantly more apoptosis was seen if the order of treatment entailed a cannabinoid-pair after a chemotherapy drug (FIG. 4b).

CONCLUSIONS

These data represented in Examples 1 to 4 and FIGS. 1 to 4 demonstrate that the combination of cannabinoids, particularly the combination of CBD with THC were able to synergistically act to reduce the cell numbers in a leukaemia cell line.

Furthermore, these data additionally demonstrate that when the cannabinoid-pairs CBD+THC are used in combination with vincristine or cytarabine a synergistic reduction in cell number and cell viability occurs. In particular the combination of CBD+THC with vincristine appeared to produce the most significant synergistic effect.

Example 4 also suggests that the cannabinoid-pair and the chemotherapeutic drug did not need to be administered at the same time to produce an effect. It was seen that administration of the cannabinoid-pair after the chemotherapeutic treatment resulted in an increase of cells undergoing apoptosis in comparison to when the cannabinoid-pair were administered prior to the chemotherapeutic drug. Such data might provide a useful indicator that in the clinical setting, where it may be difficult to administer the drugs concurrently, the administration of either the cannabinoid-pair prior to or after the treatment with the chemotherapeutic drug would provide just as good if not better results. Furthermore, priming a patient with a small dose of cannabinoid-pair before treatment with the chemotherapeutic drug, followed by the main dose of cannabinoid-pair may prove even more beneficial.

In conclusion, these data demonstrate that the combination of CBD with THC with the anti-leukaemia chemotherapeutic agents vincristine or cytarabine are effective in reducing both the cell viability of leukaemia cells. The use of such a combination may prove to be of particular clinical benefit as it would produce a better clinical outcome or reduce the amount of chemotherapeutic agent provided without a loss of activity meaning a reduction in the side effects suffered.

REFERENCES

Chou T C. Theoretical basis, experimental design, and computerized simulation of synergism and antagonism in drug combination studies. Pharmacol Rev. 2006; 58(3): 621-81.

Liu W M, Scott K A, Shamash J, Joel S and Powles T B. Enhancing the in vitro cytotoxic activity of delta-9-tetrahydrocannabinol in leukemic cells through a combinational approach. Leukemia and Lymphoma, September 2008, 49(9): 1800-1809.

Scott K A, Shah S, Dalgleish A G, Liu W M. Enhancing the Activity of Cannabidiol and Other Cannabinoids In Vitro Through Modifications to Drug Combinations and Treatment Schedules. Anticancer Research. October 2013, vol. 33, no. 10, 4373-4380

Velasco G, Sánchez C, Guzmán M. Anticancer mechanisms of cannabinoids. Curr Oncol. 2016; 23(2):523-32.

The invention claimed is:

1. A method of treating leukaemia comprising administering cannabidiol (CBD) and tetrahydrocannabinol (THC) to a subject in need thereof, wherein the leukaemia is acute lymphoblastic leukaemia (ALL) or acute myeloid leukaemia (AML).

2. The method of treating leukaemia according to claim 1, which further comprises administering a chemotherapeutic drug.

3. The method of treating leukaemia according to claim 2, wherein the CBD and THC are administered separately, sequentially or simultaneously to the chemotherapeutic drug.

4. The method of treating leukaemia according to claim 1, wherein the leukaemia is acute lymphoblastic leukaemia (ALL).

5. The method of treating leukaemia according to claim 1, wherein the type of leukaemia is acute myeloid leukaemia (AML).

6. The method of treating leukaemia according to claim 1, wherein the leukaemia is a childhood leukaemia.

7. The method of treating leukaemia according to claim 1, wherein the CBD and/or the THC are present in the form of a *Cannabis* plant extract.

8. The method of treating leukaemia according to claim 7, wherein the CBD and/or the THC are present as a highly purified extract of *Cannabis* which comprises at least 98% (w/w) of the particular cannabinoid.

9. The method of treating leukaemia according to claim 1, wherein the CBD and/or the THC are present as a synthetic compound.

10. The method of treating leukaemia according to claim 1, wherein the CBD and THC are present in a ratio of from 10:1 to 1:10 (CBD:THC).

11. The method of treating leukaemia according to claim 10, wherein the CBD and THC are present in a ratio of from 5:1 to 1:5 (CBD:THC).

12. The method of treating leukaemia according to claim 11, wherein the CBD and THC are present in a ratio of from 2:1 to 1:2 (CBD:THC).

13. The method of treating leukaemia according to claim 12, wherein the CBD and THC are present in a ratio of from 1.08:1 to 1:1.08 (CBD:THC).

14. The method of treating leukaemia according to claim 13, wherein the CBD and THC are present in a ratio of approximately 1:1 (CBD:THC).

15. The method of treating leukaemia according to claim 1, wherein the CBD and THC are present in a dose of from 0.1 to 100 mg/kg/day.

16. The method of treating leukaemia according to claim 2, wherein the chemotherapeutic drug is: cytarabine or vincristine.

17. The method of treating leukaemia according to claim 16, wherein the chemotherapeutic drug is vincristine and the type of leukaemia is lymphoblastic leukaemia.

18. The method of treating leukaemia according to claim 16, wherein the chemotherapeutic drug is cytarabine and the type of leukaemia is myeloid leukaemia.

\* \* \* \* \*